(12) United States Patent
Armbruster et al.

(10) Patent No.: US 7,790,398 B2
(45) Date of Patent: Sep. 7, 2010

(54) METHOD FOR DETERMINING EFFECTIVE PARATHORMONE ACTIVITY IN A SAMPLE

(76) Inventors: Franz Paul Armbruster, ABC Armbruster Biochemicals, Mittelstrasse 24, 67240 Bobenheim-Roxheim (DE); Heinz-Juergen Roth, c/o Labor Limbach, Im Breitspiel 15, 69126 Heidelberg (DE); Heinrich Schmidt-Gayk, c/o Labor Limbach, Im Breitspiel 15, 69126 Heidelberg (DE)

( * ) Notice: Subject to any disclaimer, the term of this patent is extended or adjusted under 35 U.S.C. 154(b) by 886 days.

(21) Appl. No.: 10/473,975

(22) PCT Filed: Apr. 3, 2002

(86) PCT No.: PCT/EP02/03659

§ 371 (c)(1),
(2), (4) Date: Feb. 23, 2004

(87) PCT Pub. No.: WO02/082092

PCT Pub. Date: Oct. 17, 2002

(65) Prior Publication Data

US 2006/0211054 A1  Sep. 21, 2006

(30) Foreign Application Priority Data

Apr. 3, 2001  (DE) .............................. 101 16 552

(51) Int. Cl.
*G01N 33/53* (2006.01)

(52) U.S. Cl. .................. 435/7.1; 435/7.2; 435/7.91; 435/7.92

(58) Field of Classification Search .............. 435/7.1, 435/7.9, 7.94, 40.5, 331, 518
See application file for complete search history.

(56) References Cited

U.S. PATENT DOCUMENTS

| | | | | |
|---|---|---|---|---|
| 5,185,128 A | * | 2/1993 | McClune et al. | 422/61 |
| 5,552,293 A | * | 9/1996 | Lindholm et al. | 435/7.23 |
| 6,187,270 B1 | * | 2/2001 | Schmitt et al. | 422/101 |

FOREIGN PATENT DOCUMENTS

| | | |
|---|---|---|
| WO | WO 96 10041 A | 4/1996 |
| WO | WO 01 44818 A | 6/2001 |

OTHER PUBLICATIONS

Clark et al. (J Biol. Chem 1990, vol. 265, p. 17405-17408).*
Maegerlein et al., Drug Reseach, vol. 48, No. 2, pp. 199-204 (1998).
Zull et al., The Journal of Biological Chemistry, vol. 265, No. 10, pp. 5671-5676 (1990).
Logue et al., Journal of Immunological Methods, vol. 137, No. 2, pp. 159-166 (1991).

* cited by examiner

*Primary Examiner*—Jacob Cheu
(74) *Attorney, Agent, or Firm*—Birch, Stewart, Kolasch & Birch, LLP

(57) ABSTRACT

Method for determining the active parathyroid hormone content in a sample, wherein the component of parathyroid hormone polypeptide chains which are oxidized at one or more sites near the PTH receptor binding structure having the amino acids 15 to 22 are specifically excluded from the content determination. Oxidation of the parathyroid hormone occurs in particular in dialysis patients, their blood plasma being exposed to an oxidation stress in the dialysis. The invention is based on the use of antibodies which bind specific conformation epitopes of the oxidised or reduced parathyroid hormone and its fragments. Further, there is provided a test system for the quantitative determination of parathyroid hormone and active fragments hereof in a sample.

11 Claims, 13 Drawing Sheets

METHOD FOR DETERMINING EFFECTIVE PARATHORMONE ACTIVITY IN A SAMPLE

Figure 1:
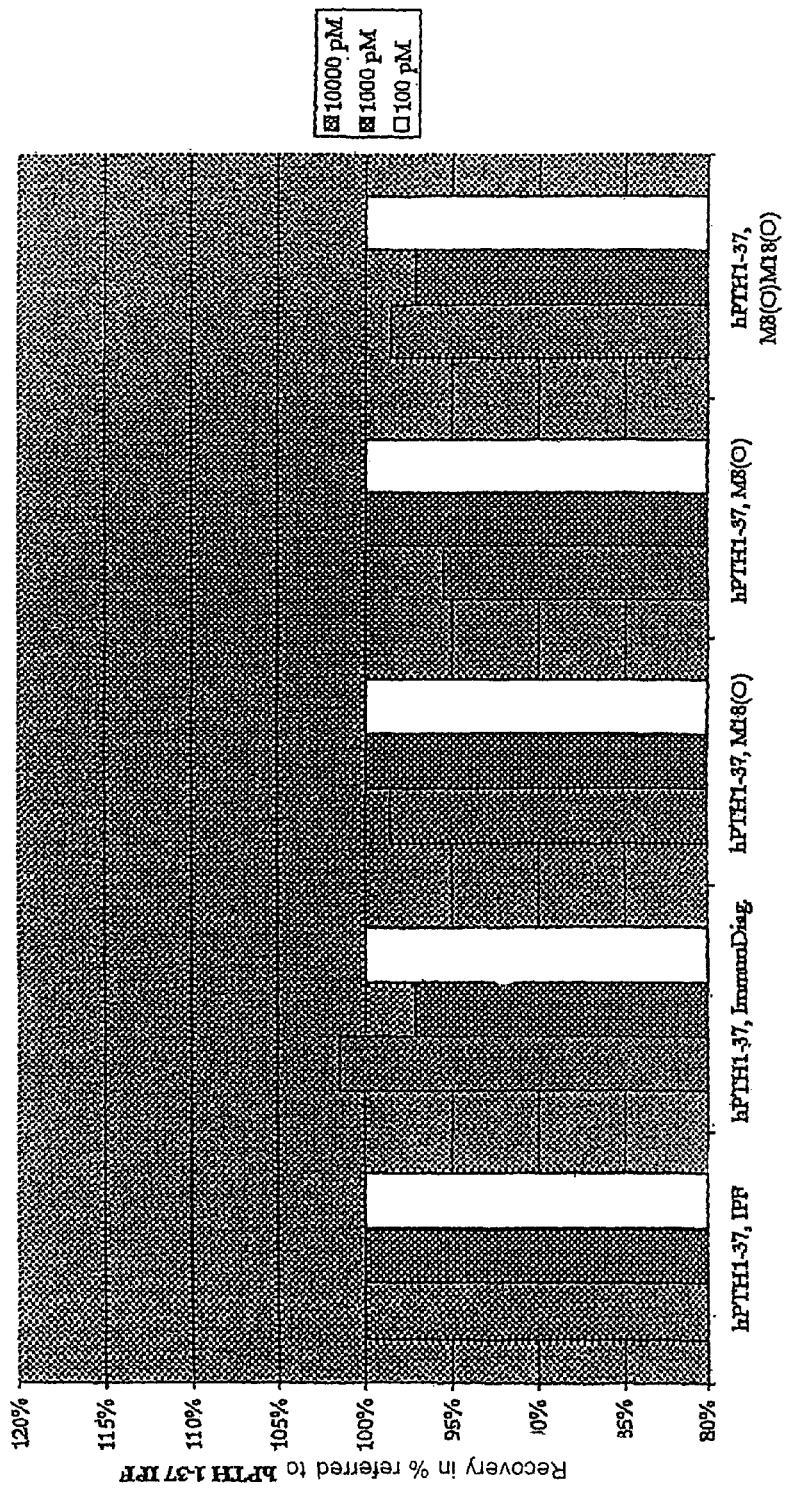

This application is the national phase under 35 U.S.C. §371 of PCT International Application No. PCT/EP02/03659 which has an International filing date of Apr. 3, 2002, which designated the United States of America.

The invention relates to an immunological method for determining the effective concentration of parathyroid hormone contained in a sample. The invention relates in particular to a test kit for the determination of the content of active parathyroid hormone and its biologically active fragments for diagnosis, etiology and treatment of disturbances of the calcium metabolism, osteopathies and hyper- or hypo-parathyroidism.

The parathyroid hormone (PTH) is formed in the parathyroid gland (Glandulae parathyroideae) and secreted into the blood circulation. In the intact form it consists of a single polypeptide chain having 84 amino acids and has a molecular weight of ca. 9500 Dalton (see SWISS-PROT: P01270, PTHY-HUMAN). Together with Vitamin-D and calcitonin it brings about the mobilization of calcium and phosphate out of the bone skeleton and increases the uptake of calcium in the intestines and the excretion of phosphate via the kidneys. The effective PTH activity in plasma or serum is thus an important diagnostic parameter and necessary for determining 1) presence and degree of hyper- or hypo-parathyroidism, 2) quantification of osteoblast activity, 3) quantification of osteoclast activity 4) monitoring of treatment with Vitamin-D and active Vitamin-D metabolites, 5) estimation of presence of aluminium, 6) estimation of a possible oestrogen deficiency in post-menopausal dialysis patients, 6) the necessary steroid or cyclosporin dosage after kidney transplantations, 7) the need for treatment and the prevention of pathological bone marrow changes, uraemic conditions and chronic kidney failure.

In the state of the art the determination of PTH is effected by means of the detection of two separated epitopes on the PTH polypeptide chain. With the introduction of specific highly sensitive immunoassays for determining the quantity of intact PTH chains in human serum there appeared to be answered all diagnostic questions in the field of calcium homeostasis, bone transformation and the responsible controlling organs such as the parathyroid gland.

However, the values so determined often do not correspond to the actually present PTH activity in the plasma or serum sample, because they often provide PTH contents which are not reconcilable with the symptoms of the patients. In the case of patients with uraemic conditions with normal bone transformation, the levels of intact PTH in serum lie mostly higher by the factor 2.5 than with patients with healthy kidneys (pathological limit in the case of patients with healthy kidneys: 65 μg PTH/L; for patients having uraemic conditions: 165 μg PTH/L serum). Further, uraemic patients with comparably high PTH values often manifest significant differences in bone transformation (Slatopolsky E et al. (2000), Kidney Int., 58, 753-761). Thus these patients often have in the serum eight to ten times increased PTH concentrations, but low normal values for bone specific alkaline phosphatase (ostase). They are thus free from symptoms of an excessive PTH activity. As possible causes there have been discussed either systematic errors in the determinations or a PTH resistance of the osteoblasts, for example due to genetically reduced expression of PTH receptor. Further, the determination of the effective PTH content in serum or plasma is made more difficult in that the hormone is broken down within minutes, in the circulation or the liver, into active and inactive fragments. Some of these fragments have an activity comparable with intact PTH (see EP-A 0 349 545; Schmidt-Gayk et al. (1999) Osteologie forum, 5, 48-58), on the other hand others work antagonistically. Thus, one knows that the fragments hPTH (3-34) and hPTH (7-34) can inhibit the effects of PTH (Suva et al. (1987) Science, 237, 893ff; EP 0 451 867).

Moreover, "non-(1-84)" large PTH fragments have been suspected to lie behind the erroneous determinations (LePage R. et al. (1998) Clin. Chem., 44, 805-809). The designation "Large PTH fragment" is used generally for fragments which contain at least the polypeptide chain with the amino acids 39-84 and epitopes of the N-terminal fragments hPTH (1-33), hPTH (1-34), hPTH (1-37) or hPTH (1-38) but from which the N-terminal amino acids 1 to 3 are missing. WO 96/10041 teaches that after loss of the N-terminal amino acids serine and valine the PTH fragments are no longer active. The characterising of various immunological tests with synthetic fragments of the type hPTH (7-84) showed that these as a rule also determine the inactive large PTH (7-84) fragment (John M R et al. (1999), J. Clin. Endocrinol. Metab., 84. 4287-4290; Gao P et al. 2000, Poster M455, ASBMR $22^{nd}$ Annual Meeting; Roth H J et al. (2000), Poster P1288; $11^{th}$ International Congress of Endocrinology, Sydney). The co-determination of inactive large PTH fragments was thus made responsible for the discrepancy between measured PTH concentration and clinical findings. It was suspected that intact PTH molecules compete with the large PTH fragments for the binding sites on the PTH receptor and that depending upon the concentration of CAP (Cyclase activating PTH—biologically active) or CIP (Cyclase Inhibiting PTH—biologically inactive, receptor blocking) different cell activations occurred.

It is object of the invention to make available a method for the quantative determination of the effective PTH content of a sample.

This object is achieved by means of the method according to claim 1. Further advantageous embodiments of the method are indicated in the subclaims.

The method in accordance with the invention for quantitative determination of the PTH content in a sample is characterized in that intact PTH polypeptide chains and N-terminal intact fragments hereof having the PTH receptor binding structure (15 to 22), which are oxidised at one or more sites neighbouring the PTH receptor binding structure (15 to 22), are excluded from the content determination. In other words there are excluded from the determination of the PTH activity or the effective PTH content all PTH polypeptide chains and fragments hereof which are oxidised at methionine-8 or -18 or at both positions. This is effected through the use of antibodies which bind to a PTH epitope which is formed from at least one oxidised methionine group at position 8 and/or 18, or of antibodies which bind specifically PTH polypeptide chains or fragments hereof which are oxidised at methionine 8 and/or 18, or antibodies which can distinguish between specific conformation epitopes of the oxidised and of the "native" non-oxidised parathyroid hormone. It is this ensured that there are excluded from the determination: inactive large PTH fragments of the types hPTH (7-84) or hPTH (3-84), oxidised intact hPTH (1-84) and oxidised N-terminal intact oxidised hPTH (1-34) fragments of the type ox-hPTH (1-34) or ox-hPTH (1-37), which contain the receptor binding structure PTH (15-22).

In accordance with the invention, the antibodies are obtainable via a purification or selection on parathyroid hormone which is oxidised at position 8 and/or 18. The antibodies can be obtained through immunization with synthetic or specifically oxidised PTH fragments (Logue F C et al. (1991), Ann. Clin. Biochem., 28 160-166; Journal of Immunological Methods, 39, 159). For example, synthetic PTH (1-34) can be oxidised at the methionines 8 and 18 through the addition of $H_2O_2$ and put to use for the immunization. Particularly preferred are monoclonal antibodies against methionine-8, which apparently is oxidized first.

In an embodiment of the method in accordance with the invention, the parathyroid hormone and its potentially active fragments are chemically post-oxidized and/or post-reduced and the content of intact parathyroid hormone and its active fragments is determined by a double determination (before and after). In a further embodiment, there is separately and additionally determined the content of oxidised intact parathyroid hormone and fragments hereof in the sample and calculated via the simultaneous determination of total PTH and the content of non-oxidized PTH and its biologically active fragments.

In a particularly preferred embodiment of the method there are added antibodies against parathyroid hormone oxidized at position 8 and/or 18, for masking the oxidized parathyroid hormone, so that exclusively non-oxidized or biologically active parathyroid hormone and its fragments are bound by primary and secondary antibodies. The method in accordance with the invention then includes the following steps: treating the sample with an antibody which recognizes an epitope in which parathyroid hormone oxidized at position 8 and/or 18 is involved; treatment of the sample with an antibody which recognizes an epitope which is formed from the N-terminal amino acids 1 to 3 of the parathyroid hormone; treatment of the sample with an antibody which recognizes an epitope in the region of the receptor binding structure (amino acids 15 to 22) of human parathyroid hormone and which cannot bond when the antibody has already bonded in the region of the oxidized methionine 8 and/or 18, and determination of the number of the molecules which are recognized by the two antibodies. Preferably, here the binding of the two antibodies takes place in the presence of the 0.05 to 0.1 weight percent of a mild detergent such as Tween™20 or Triton™X-100. In accordance with the invention, in a particularly preferred embodiment, the sample is thus first treated with antibodies against oxidized parathyroid hormone, so that antibodies which bind in the region of receptor binding site of the parathyroid hormone cannot bind to the oxidized PTH polypeptide chain. The person skilled in the art will recognize that the antibody for masking of oxidized parathyroid hormone and fragments hereof should better, be of a different type than the antibody for forming or detecting the sandwich complex. The antibodies employed as captors and tracers, may, as the skilled person knows, also be functionally exchanged.

In a further embodiment at least one of the antibodies carries a marking, selected from a fluorescing or chemiluminescing group or an enzyme for catalysing a detection reaction. Preferably one of the antibodies is a monoclonal antibody marked with a ruthenium complex, which recognizes an epitope in the region of the amino acids 15 to 22 or 26 to 32. One of the antibodies may also be biotinylated and bonded via streptavidin to a solid phase. In the method there can further be employed antibodies which bind to the PTH polypeptide chain with amino acids 4 to 14 or 15 to 35v39. An antibody which recognizes an epitope in the range of amino acids 15 to 22 is particularly preferred since on the one hand this epitope lies in the range of the receptor binding structure, on the other hand such an antibody can distinguish, due to the methionine 18, between oxidized and native hPTH.

The test system in accordance with the invention for the quantitive determination of parathyroid hormone and fragments hereof in a sample includes in one embodiment antibodies (captor antibodies) bound to a phase, which antibodies bind in or near the PTH receptor binding structure of the parathyroid hormone and—for masking—free (unbound) antibodies, which bind the epitopes of the parathyroid hormone having oxidized methionine 8 and/or 18. The antibodies can be purified through affinity chromatography, for example via their binding to methionine 8 and/or 18 of the oxidized parathyroid hormone. As tracer antibodies there are employed antibodies against the N-terminal amino acids 1 to 3 of the parathyroid hormone (in the reduced structure). Captor and tracer antibodies may also be exchanged.

The invention further relates to the diagnosis of oxidation stress in dialysis patients, whereby an in vitro test for the quantitative determination of parathyroid hormone and it active fragments in accordance with the invention is put to use.

Even though one knew from experiments with synthetic PTH fragments that oxidized parathyroid hormone or oxidized parathyroid hormone fragments are biologically inactive, one did not imagine that this oxidation could assume physiologically relevant levels and prevent the determination of the true physiological PTH activity in a sample. Thus in some conventional test methods there were added reduction means for stabilizing the antibodies in the sample buffer, in others a subsequent partial oxidation of the PTH molecule was tolerated.

The invention also relates in an embodiment to a method for a diagnosis and determination of the extent of a hypo- or hyper-parathyroidism, the etiology of calcium metabolism disturbances, osteopathies, kidney failures and conditions which arise from a disturbed homeostasis of the calcium and phosphate contents of the blood. Further, in accordance with the invention the direct production of N-terminal PTH fragments, so far as this arises, is also detected. This means that the PTH diagnosis in accordance with the invention detects along with intact active parathyroid hormone also directly produced, biologically active PTH fragments.

Oxygen is essential for aerobic life but at the same time is the most important precursor molecule of free reactive oxygen species (ROS) which through their reaction with proteins, lipids and nucleic acids damage the cells and through the oxidation of reactive amino acids can alter proteins in their structure. Many publications have been concerned with the effect of oxidation stress and the influence of "advanced glycation end products" on the pathogenesis of complications in the case of chronically kidney insufficient patients (Martin-Mateo M C et al. (1999), Ren. Fail., 21, 155-167; Hasselwander O et al. (1998), Free Radic. Res., 29, 1-11; Zoccali C et al. (2000), Nephrol. Dial. Transplant., 15, Suppl. 2; Canaud B et al. (1999), Blood Purif., 17, 99-106). Dialysis patients are in comparison to normal persons much more strongly affected by oxidative stress. Various working groups have investigated oxidized parathyroid hormone and its biological activity (Alexiewicz L M et al. (1990), J. Am. Soc. Nephrol., 1, 236-244; Zull J E et al. (1990), J. Biol. Chem., 265, 5671-5676; Pitts T O et al. (1988), Miner. Electrolyte Metab., 15, 267-275; Horiuchi N. (1988), J. Bone Miner. Res., 3, 353-358; Frelinger A L et al. (1986) Arch. Biochem. Biophys., 244, 641-649; Galceran T et al. (1984) Endocrinology 115, 2375-2378; Frelinger A L et al. (1984), J. Biol. Chem., 259, 5507-5513; O'Riordan J L H et al. (1974), J. Endocr., 63, 117-124; Logue F C et al. (1991), Ann. Clin. Biochem., 28, 160-166; Logue F C (1991b), J. Immun. Meth., 39, 159). Oxidation stress in dialysis patients and its consequence for PTH diagnosis have, however, not so far been investigated and recognized.

It has now been found that the conventional methods of determination, in each case depending on the test kit and antibodies, detect both bioactive (native or reduced) intact PTH and if applicable its fragments and also oxidized PTH and if applicable its fragments, and thus falsely determine the effective level of parathyroid hormone.

Further, it has been found that the postulated large PTH fragments, insofar as they arise at all, have no biological significance: rather that the discrepancy between measured PTH content and medical determination arises at least partly from the oxidation stress to which the dialysis patient is subject. The effective PTH content in a plasma or serum sample is namely dependent upon the oxidation stress and the oxidation stress is at the same time a cause of pathological conditions.

The invention relates further to a method in which a first captor antibody is bonded to a solid phase. The second tracer antibody may carry a marker, e.g. a fluorescent or chemiluminescent group, or may be conjugated with an enzyme such as alkaline phosphatase or peroxidase. The method is effected in accordance with the invention in a per se known immunoassay, preferably in an ELISA, ECLIA, IEMA, IRMA, ILMA or LIA. The binding of the two antibodies to the PTH is preferably effected in the presence of 0.05 to 0.1 weight percent of a mild detergent such as Tween™20 or Triton™X-100 so that a folding of the N-terminal epitope PTH (1-3) to the PTH receptor binding structure is prevented, or in order to keep the N-terminal epitope PTH (1-3) accessible for binding with the antibody. Since for the biological activity and the folding of the PTH both the receptor binding structure and also the amino-terminal epitope PTH (1-3) are necessary, these two structures probably interact with one another. Through the presence of a mild detergent, in the above-mentioned embodiment with antibodies against hPTH (1-3), the sensitivity and accuracy of the assay can be significantly improved.

In an embodiment of the method a known aliquot of the sample is further treated with antibodies which bind to the PTH sequences between amino acids 4 to 14 and/or 15 to 37. The number of molecules in a sample which are bound by antibodies against the epitope PTH (1-3) and the receptor binding structure of the PTH, and the number of molecules which are bound by the antibodies against the PTH regions 4 to 14 and 15 to 37, are then placed in relationship one to another and the biologically effective PTH activity determined.

The invention further relates to a diagnosis system for the determination of the PTH activity in a sample, which system is characterized by antibodies which recognize specifically the N-terminal epitope with the amino acids 1 to 3 and antibodies which bind to the region of the PTH receptor binding structure. In a further embodiment the diagnosis system further. has antibodies which bind in the region between amino acids 4 to 14. In a third embodiment the system includes antibodies which bind in the section between amino acids 24 and 37 of the parathyroid hormone or on the middle (53 to 68) or the C-terminal (53 to 84) section of the PTH polypeptide chain.

In contrast to earlier immunoassays, the method in accordance with the invention takes into account the PTH activity also of the non-intact PTH fragments and that apparently intact PTH is biologically inactive when the last or last two amino terminal amino acids of the parathyroid hormone are missing or when one or both methionines at position 8 and 18 of the N-terminal fragments are oxidized. PTH fragments which have neither a receptor binding structure with the amino acids 15 to 22 nor an intact N-terminal epitope PTH (1-3) have no agonistic or antagonistic activity.

Conventional immunological tests for the quantative determination of intact parathyroid hormone or hPTH (1-37) yield false activity values if a physiological activity is concluded upon only from the presence of two epitopes. Conventional methods do not take into account that the correct folding or the binding to the PTH receptor is dependent upon an intact amino-terminus with the amino acids serine and valine and that the methionine groups at position 8 and 18 near the PTH receptor binding structure must not be oxidized. The invention rests in particular on the discovery that the oxidation of PTH at the above-mentioned positions, in particular in the case of dialysis patients, can be considerable and of diagnostic significance. The fragments hPTH (7-84), hPTH (3-84) or hPTH (4-37), so far as they are present, determined in conventional tests as active PTH have no or no measurable antagonistic activity. Test systems on the basis of antibodies against the middle section (53-68) or the C-terminal (53-84) section overlook the fact that some patients directly produce biologically active PTH fragments of the type hPTH (1-37), hPTH(1-32~36) or hPTH(1-38).

Immunological methods on the basis of antibodies against hPTH(1-3) or hPTH(1-6), or against peptides from the hPTH (1-37) fragments, also reflect false activities since there are determined not only the biologically active (reduced) structure units. With polyclonal antibodies or antisera against the N-terminal peptide having the amino acids 1 to 5 or 6 in part even antagonistically effective fragments are recognized as active PTH fragments.

The method in accordance with the invention thus makes available to the doctor a PTH activity value which indicates the physiological effects of the native (reduced) parathyroid hormone and its active fragments. It recognizes also patients hyperparathyroidism who have normal or reduced contents of intact hPTH(1-84) in the serum and directly secrete PTH fragments such as hPTH(1-37) and hPTH(1-38) into the bloodstream.

The method in accordance with the invention for determining the activity of PTH and its fragments in a sample can be realized as EIA, ELISA, RIA, IRMA, LIA or ICLIA, ILMA, FIA or IFMA, as a manual test system or preferably in a version adapted to automatic systems, in liquid phase or solid phase techniques.

Figure 2:
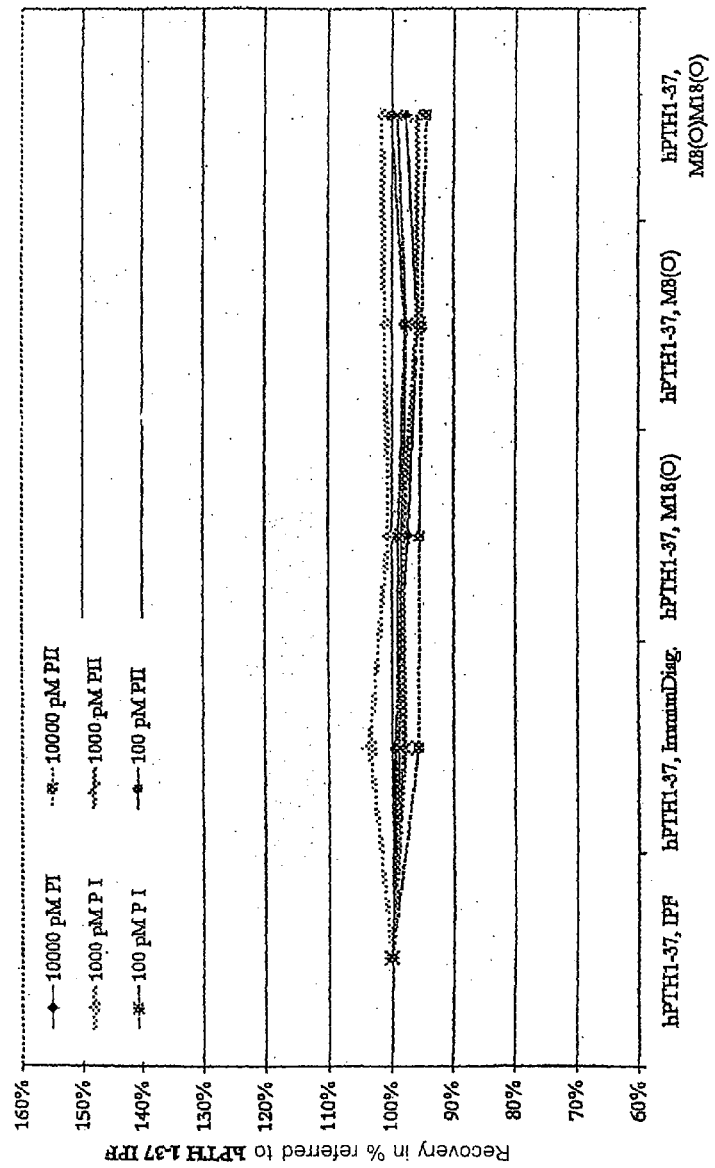
Figure 3:
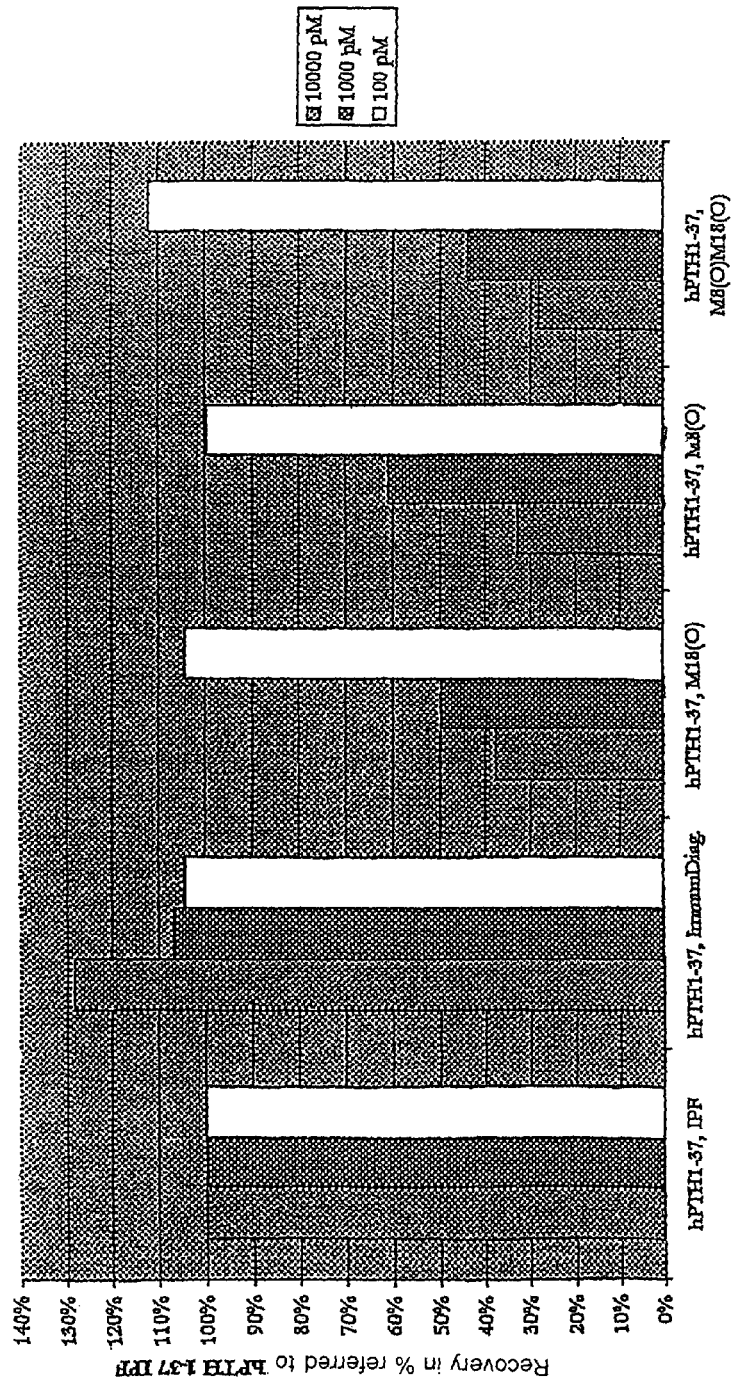
Figure 4:
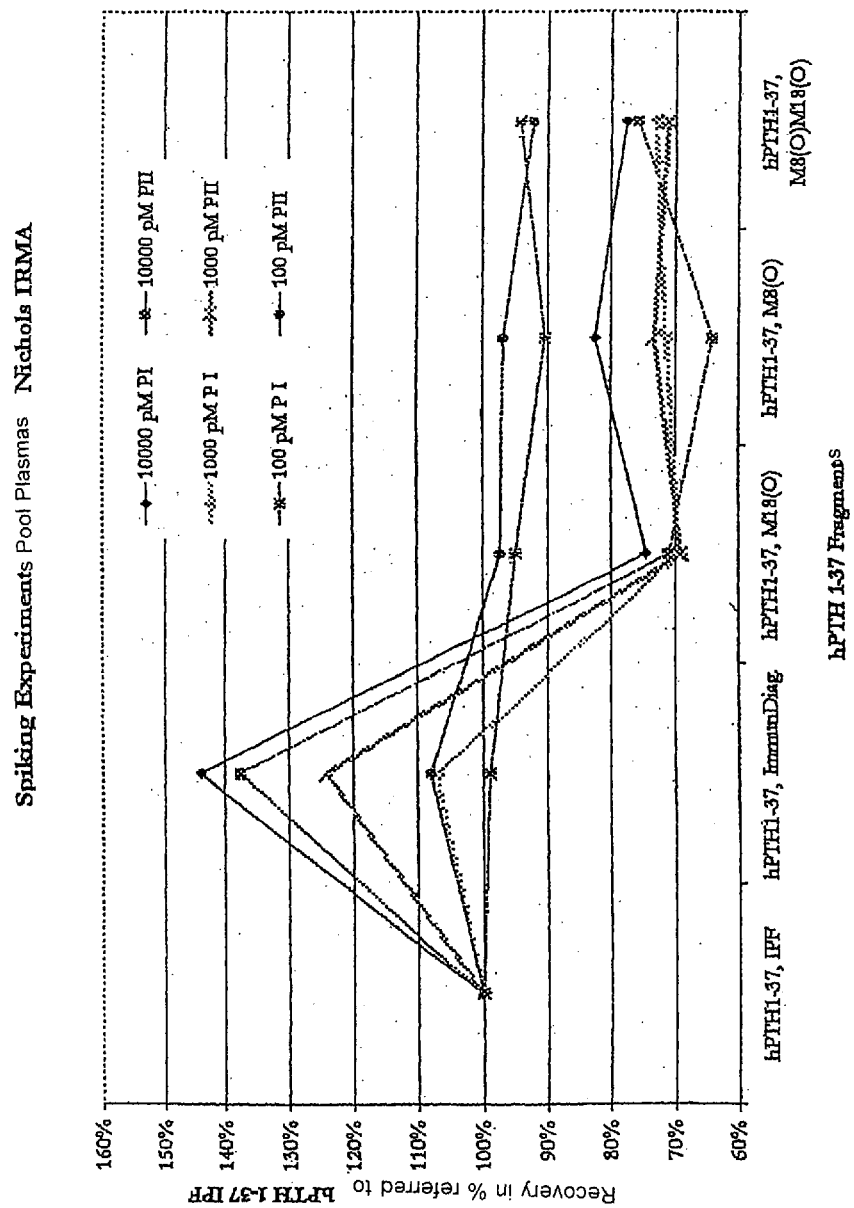
Figure 5:
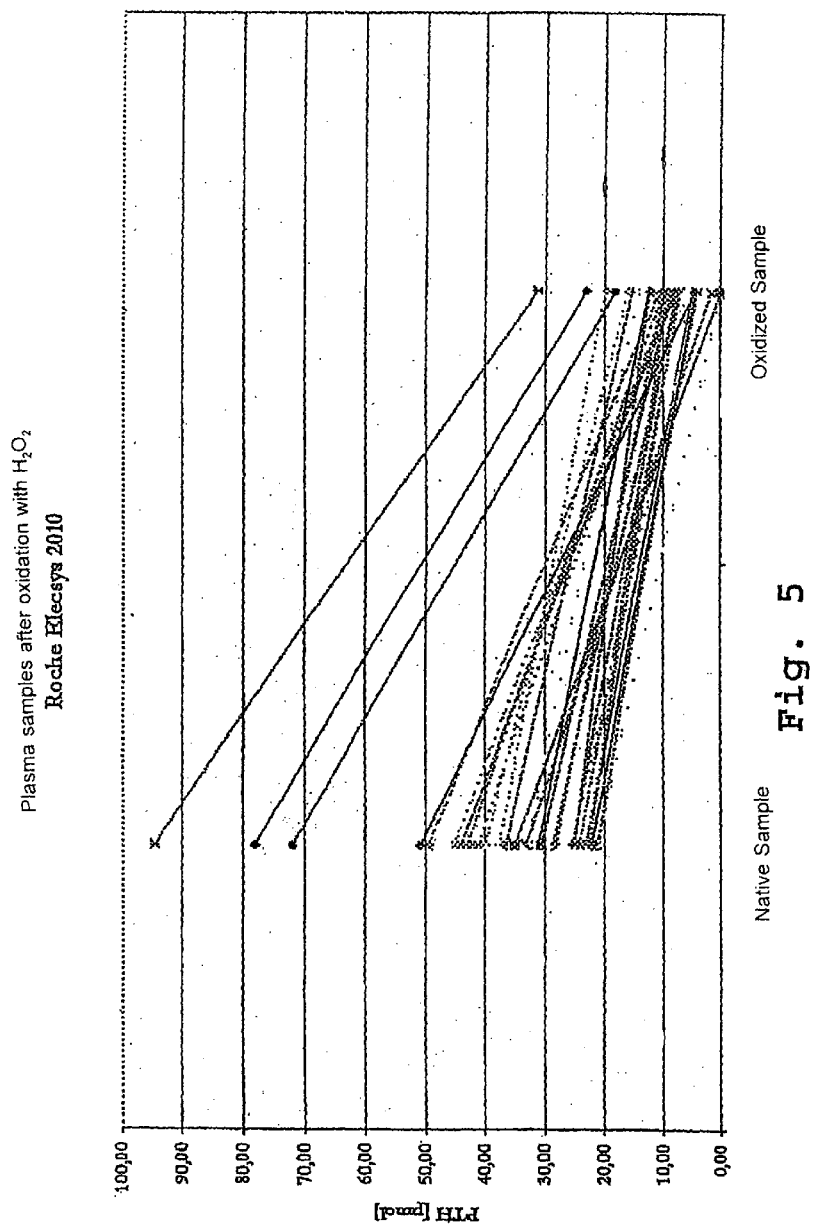
Figure 6:
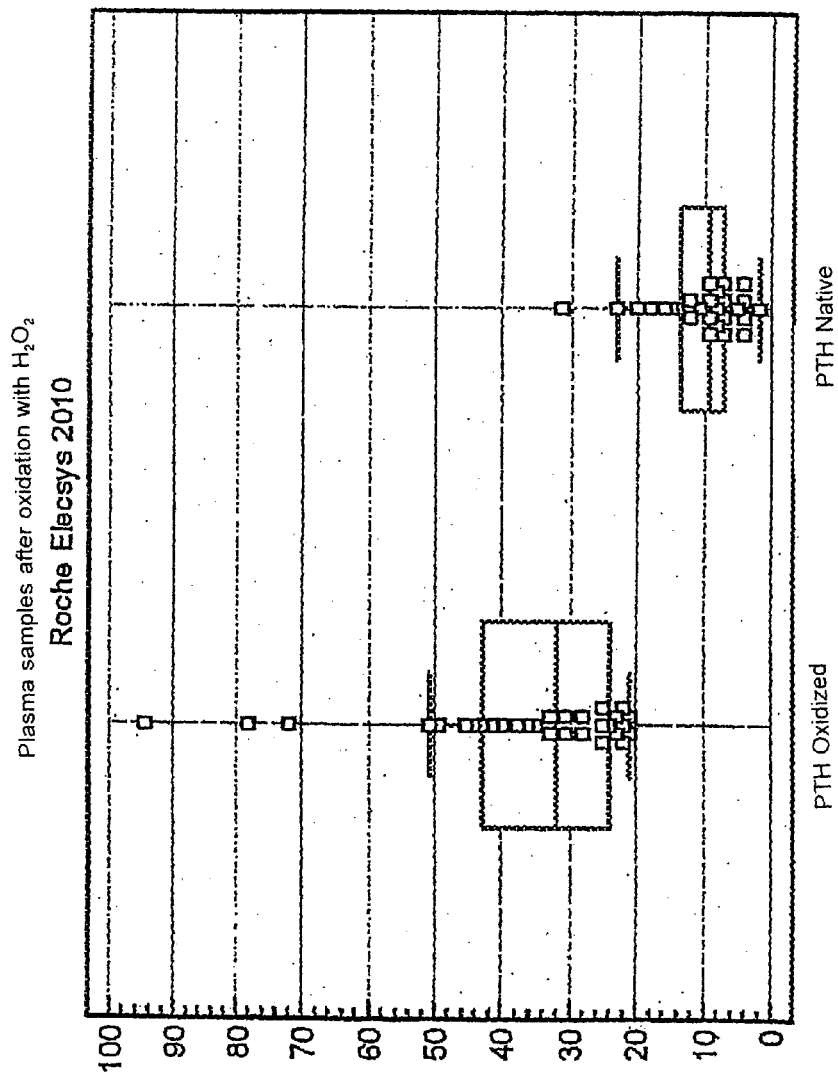
Figure 7:
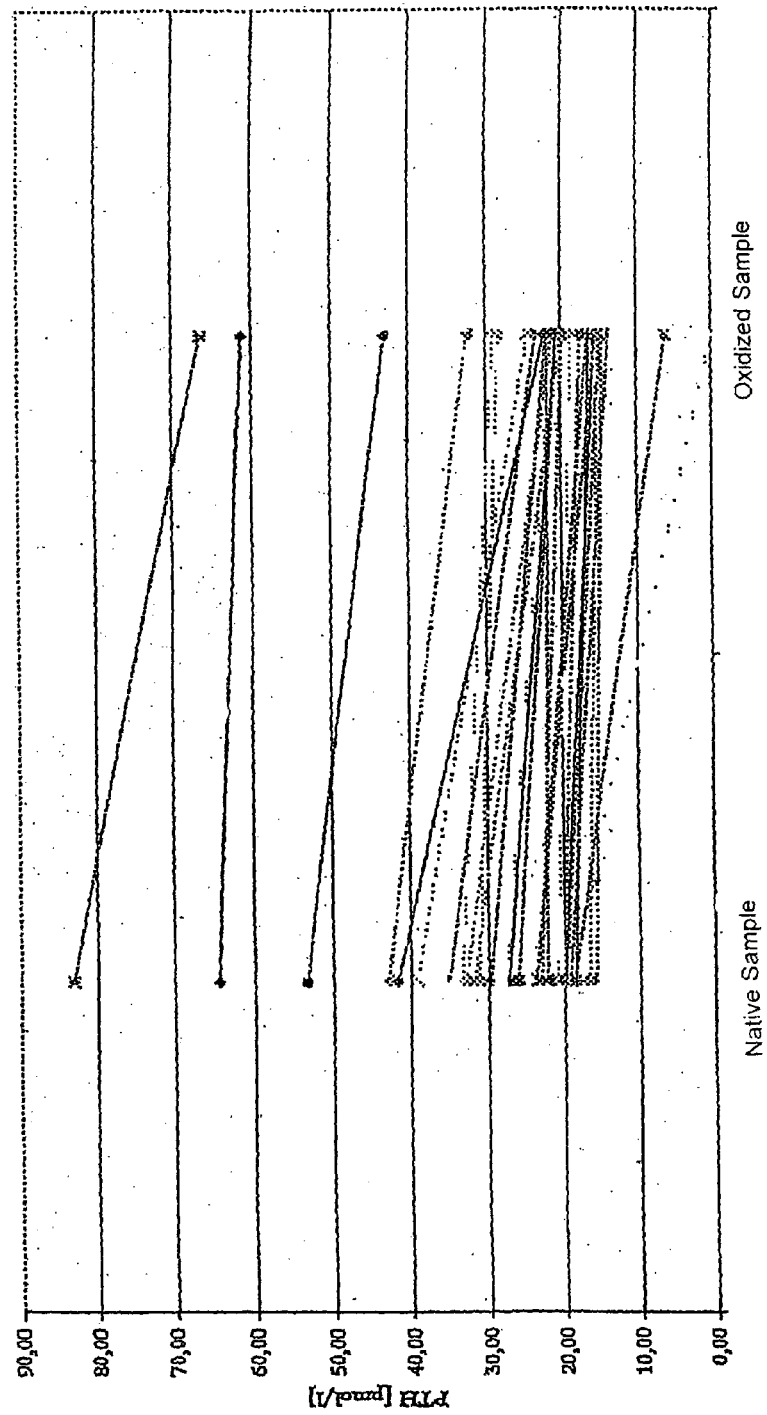
Figure 8:
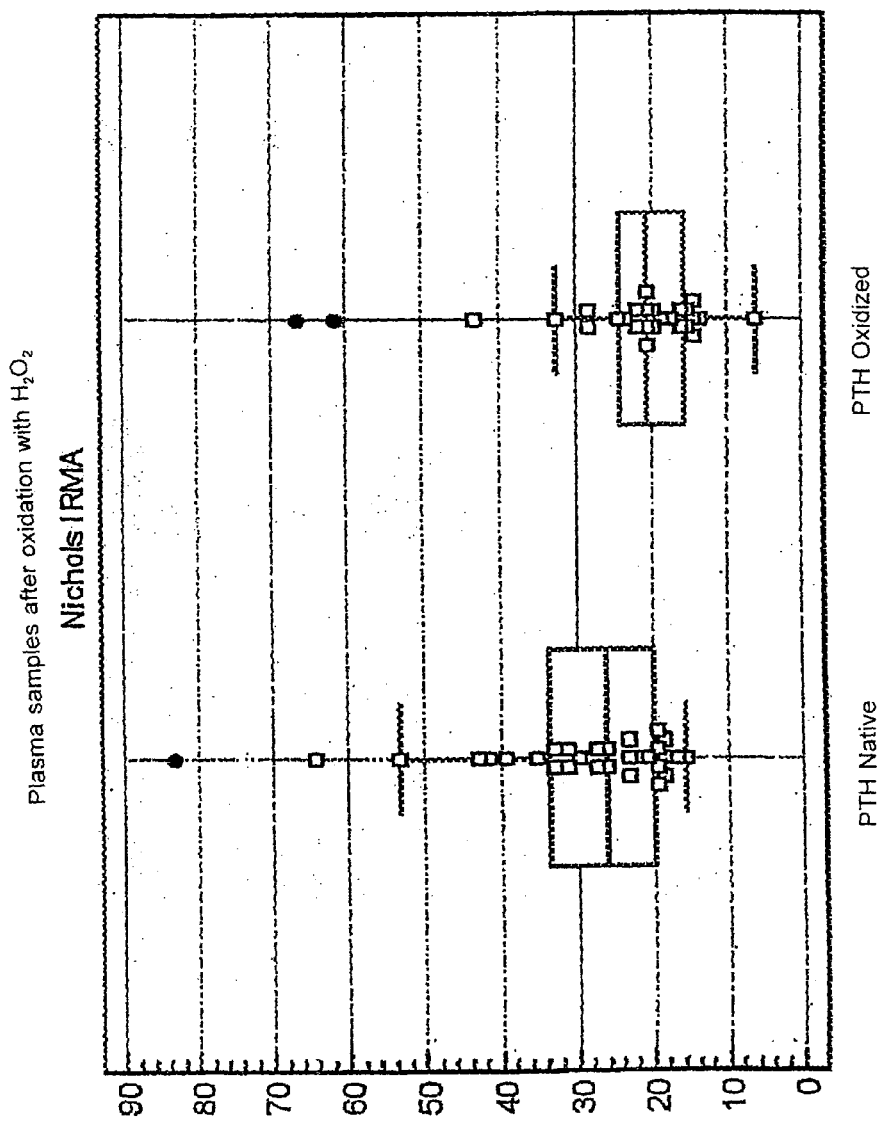
Figure 9:
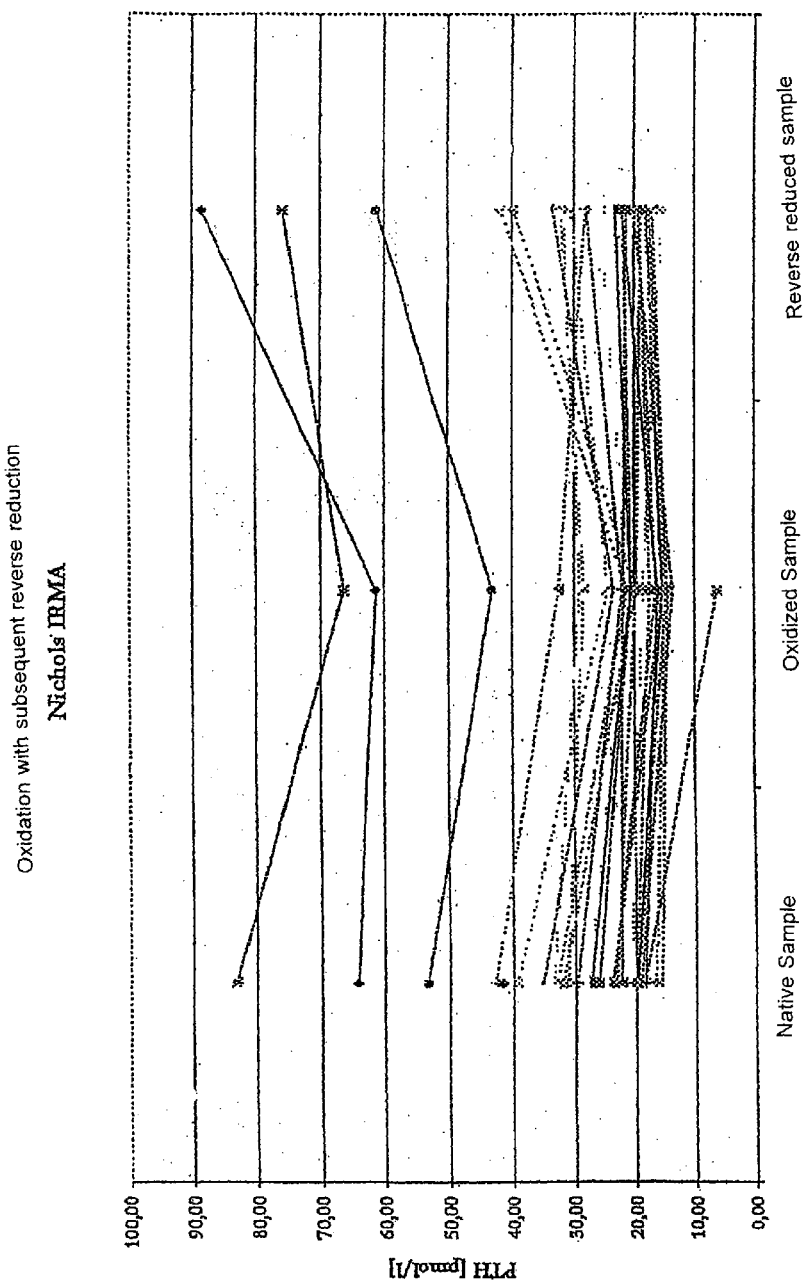
Figure 10:
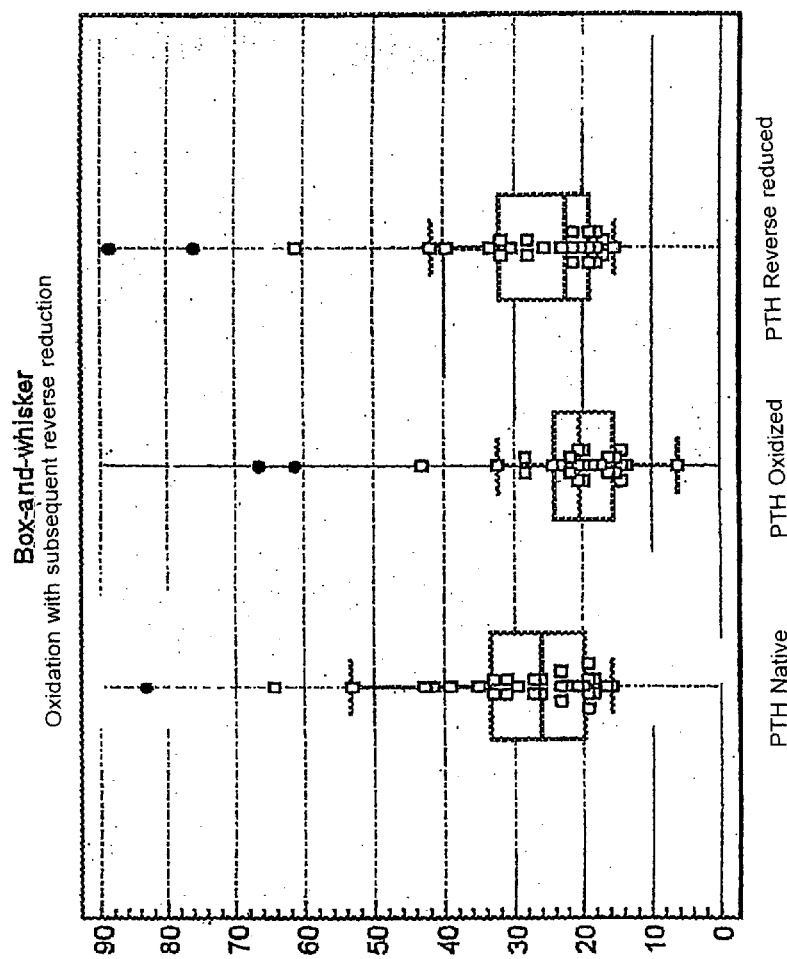
Figure 11:
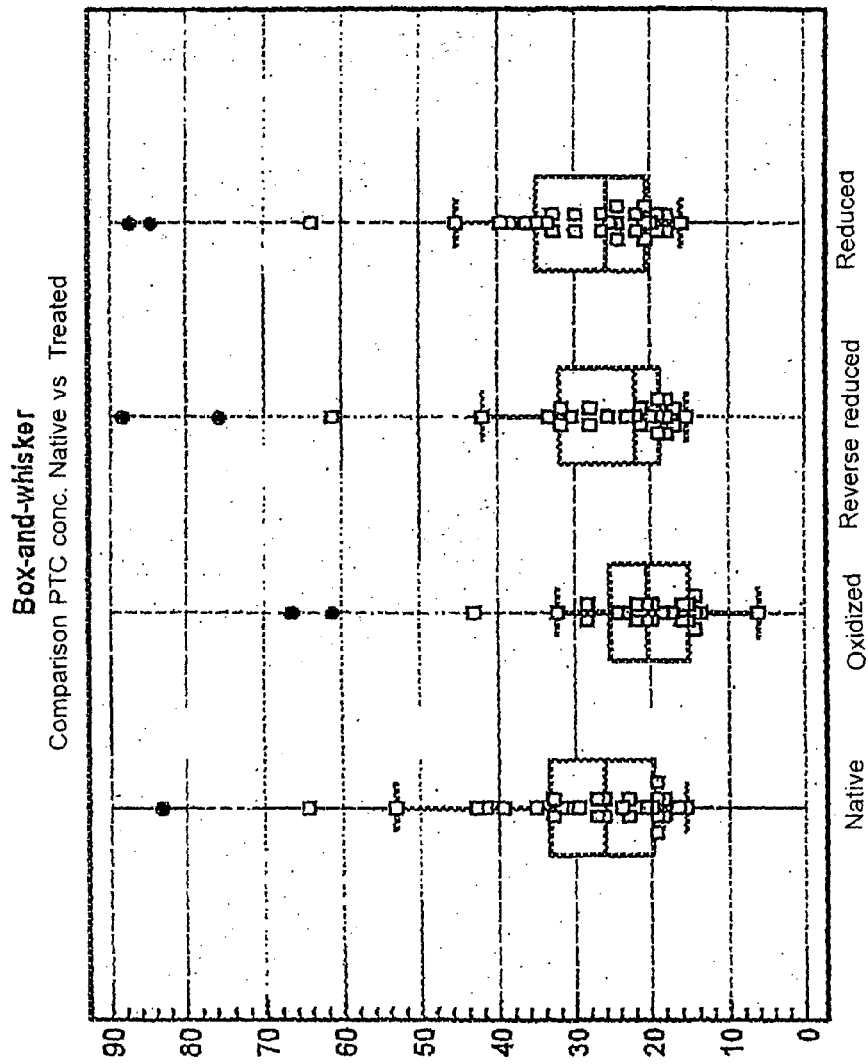
Figure 12:
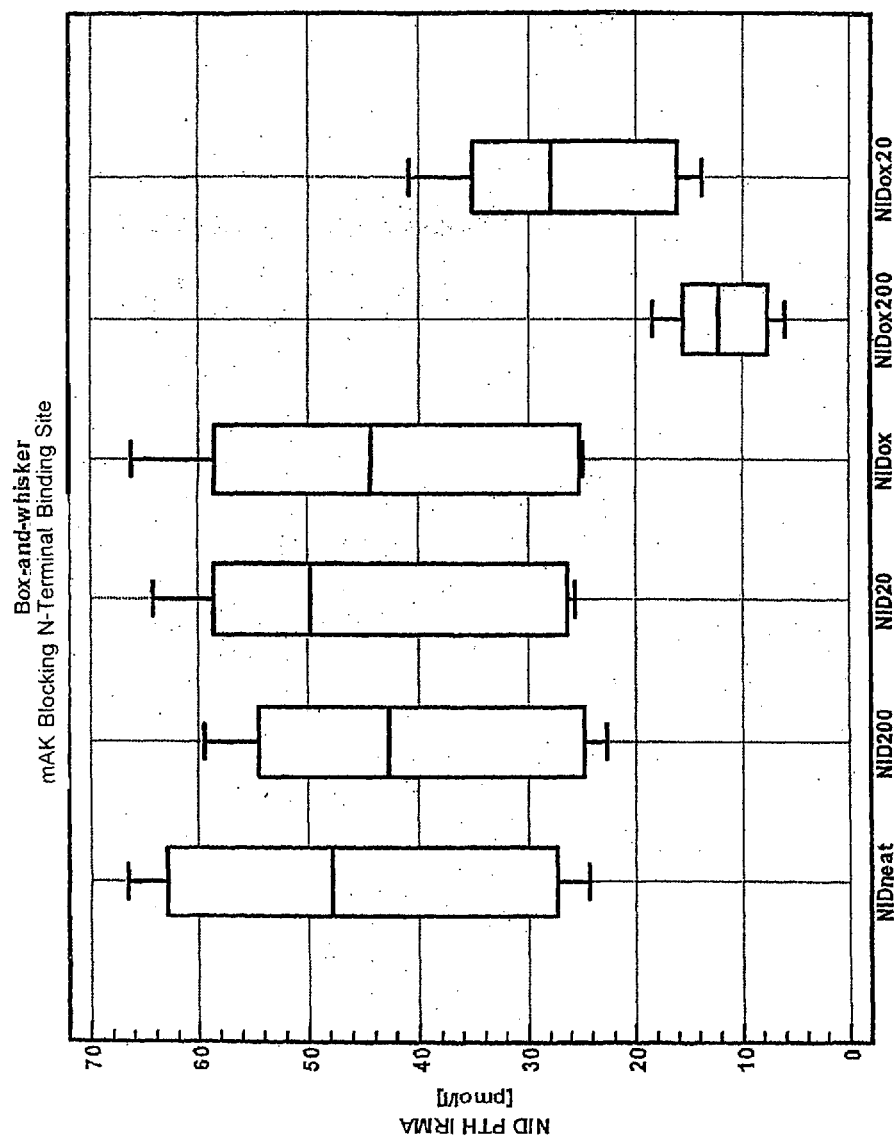
Figure 13:
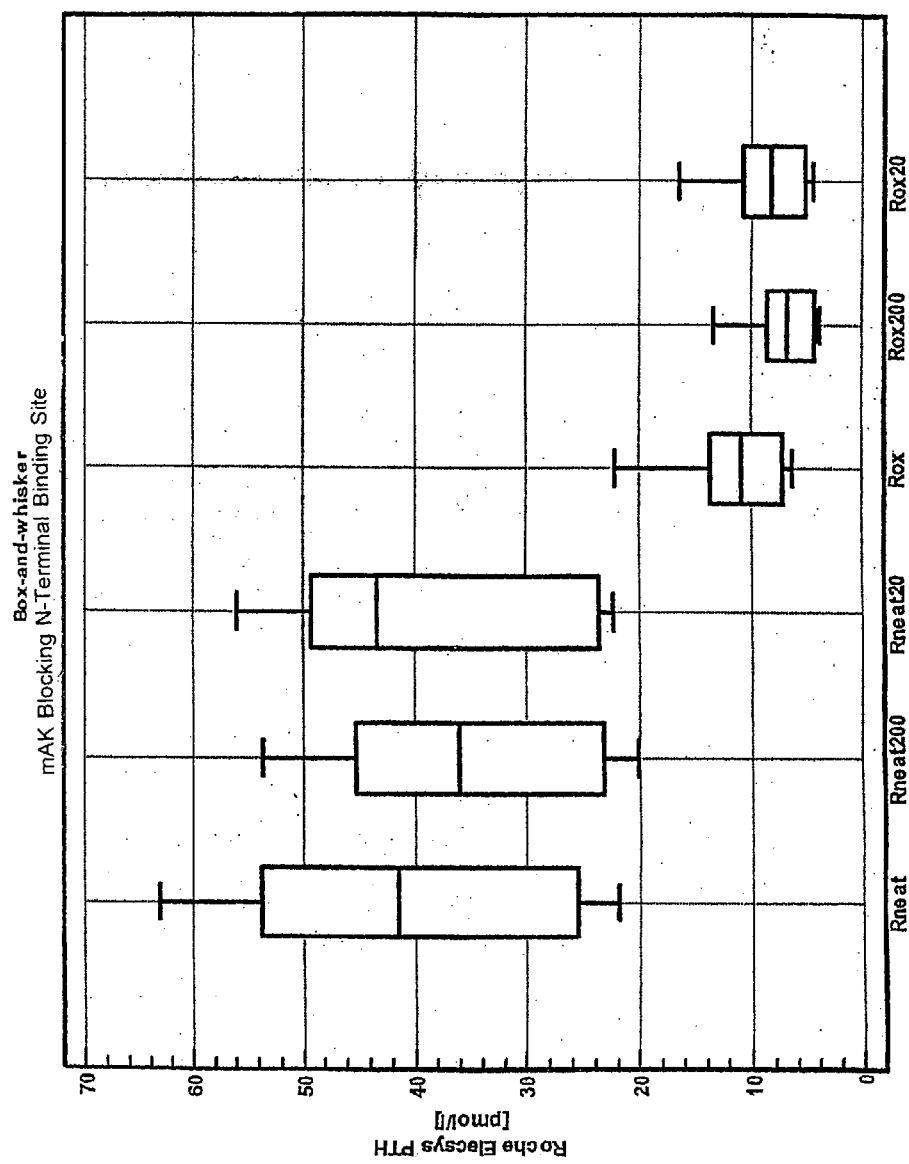

Further advantages, features and embodiments of the invention are provided through the following examples and the accompanying drawings. There is shown:

FIG. 1 a diagram with results (test system: Elecsys™2010 of Roche Diagnostics GmbH, Mannheim) of spiking experiments on PTH standard;

FIG. 2 a diagram with results (Elecsys™2010 of Roche Diagnostics) of spiking experiments on pool plasmas;

FIG. 3 a diagram with results (test system: PTH-IRMA of the Nichols Institute, U.S.A.) of spiking experiments on PTH standard;

FIG. 4 a diagram with results (PTH-IRMA of the Nichols Institute) of spiking experiments on pool plasmas;

FIG. 5 a diagram with measured values (Roche Elecsys™2010 of the plasma samples after oxidation with $H_2O_2$;

FIG. 6 a diagram with percentage measurement values (Roche Elecsys™2010) of the plasma samples after oxidation with $H_2O_2$;

FIG. 7 a diagram with measurement values (PTH-IRMA of the Nichols Institute) of the plasma samples after oxidation with $H_2O_2$;

FIG. 8 a diagram with percentage measurement values (PTH-IRMA of the Nichols Institute) of the plasma samples after oxidation with $H_2O_2$;

FIG. 9 a diagram having measurement values (PTH-IRMA of the Nichols Institute) after oxidation and reverse reduction of the samples;

FIG. 10 a diagram with percentage measurement values (PTH-IRMA of the Nichols Institute) after oxidation and reverse reduction of the samples;

FIG. 11 a diagram with percentage measurement values (PTH-IRMA of the Nichols Institute) after oxidation and direct reduction of the samples;

FIG. 12 a diagram with percentage measurement values (PTH-IRMA of the Nichols Institute) of a plasma sample with and without oxidization and after addition of monoclonal antibody against oxidized parathyroid hormone;

FIG. 13 a diagram with percentage measurement values from a plasma sample (Roche Elecsys™) with and without oxidization and after addition of monoclonal antibody against oxidized parathyroid hormone.

EXAMPLES

Example 1

Biological Effect of Large PTH Fragments

It was investigated whether the large PTH fragments, postulated in the state of the art, occur in human serum and have an antagonistic effect on the PTH receptor. The immunoassays employed were based upon antibodies which do not cross-react with synthetic hPTH(7-84) (Bachem AG), so that the measurement values should indicate the true concentration of intact active hPTH in human serum. These values were compared with parameters for bone transformation. The production of the large PTH fragments is, in accordance with the state of the art, regulated via a feedback mechanism and in the case of increased or reduced need the stimulation or suppression of the parathyroid gland leads to an adequate expression. At the present time there are known two test systems for the quantative determination of PTH which have no clinically relevant cross-reactivity with the synthetic large PTH fragment hPTH(7-84). These are the Elecsys™2010 PTH immunoassay of Roche Diagnostics GmbH, Mannheim and the CAP-PTH-IRMA of the company Scantibodies. The electrochemiluminescence immunoassay (Elecsys™ of Roche Diagnostics GmbH, Mannheim) is based upon a monoclonal captor antibody against an N-terminal PTH epitope corresponding to the amino acids 26-32 and a ruthenium complex marked tracer antibody against a C-terminal hPTH epitope corresponding to the amino acids 55-64. The employed synthetic large hPTH(7-84) fragment (Bachem AG) is not recognized by the captor antibody of the Elecsys™2010 PTH immunoassay, so that it must recognize a tertiary folding structure or is a so-called conformation antibody. Probably, the large hPTH(7-84) fragment employed (Gao P et al. 2000, Poster M455, ASBMR 22nd Annual Meeting, Roth H J et al. (2000), Poster P1288; 11th International Congress of Endocrinology, Sydney), as the present results make evident, was oxidized in the course of synthesis or storage. The captor antibody of the Elecsys™2010 PTH immunoassay probably does not bind only oxidized hPTH(7-84), but does bind reduced PTH(7-84). The CAP-PTH-IRMA of the company Scantibodies employs polyclonal antibodies against the N-terminal hPTH(1-6) which could not bind the large PTH (7-84) fragments.

Along with the determination of intact PTH using various immunoassays (Nichols IRMA, Roche Elecsys™2010, DUO-PTH Scantibodies, PTH-Immundiagnostik) there were also determined the bone marker BAP (ostase) as a formation marker and TRAP5b as resorption marker. The results are indicated in the following Table 1.

TABLE 1

Correlation of bone growth and reduction markers with PTH measurement values

| Dependent variable Y | Independent variable X | Correlation coefficient/n= |
|---|---|---|
| BAP (Ostase) | PTH CAP Scan. | 0.484 n = 96 |
| BAP (Ostase) | PTH Elecsys2010 | 0.474 n = 96 |
| BAP (Ostase) | PTH Nichols | 0.485 n = 96 |
| TRAP5b | PTH CAP Scan | 0.511 n = 95 |
| TRAP5b | PTH Elecsys2010 | 0.510 n = 95 |
| TRAP5b | PTH Nichols | 0.524 n = 95 |
| PTH CAP Scan | PTH Elecsys2010 | 0.966 n = 103 |
| PTH CAP Scan | PTH Nichols | 0.979 n = 103 |

The correlations of the values of the growth and reduction markers and the PTH contents in the serum show no significantly greater correlations for the more specific tests ("no cross reactivity to large PTH fragments") in comparison to the IRMA of the company Nichols Institute. Amongst one another the correlation of the individual PTH assays is, as has also been shown in other studies, excellent. This shows that none of the known test systems provide satisfactory results.

Example 2

Oxidation and Reduction Experiments

It was investigated whether and to what extent the Elecsys™2010 PTH test and the Nichols Intact PTH test recognize native or oxidized PTH.

The Nichols Intact PTH Assay (Nichols Institute, San Juan Capistrano, Calif., U.S.A) is a double binding immunoradiometry assay (IRMA) with two polyclonal goat antibodies. The captor antibody, immobilized in plastic beads, binds only in the middle or C-terminal section of the hPTH (anti-hPTH (39-89)). The second detection antibody, marked with $^{125}$Iodine, recognizes an epitope in the N-terminal section of the PTH (anti-hPTH(1-34)). The sample was incubated at the same time with the antibody coated beads and the $^{125}$Iodine marked detection antibody overnight (12±2 h) at room temperature. After the incubation, the beads were washed and the radioactivity adhering to the solid phase measured in a gamma counter (LKB1277 Gamma Master from Perkin-Elmer). The dose measurement curve (MultiCalc Software) between bound radioactivity and concentration in the sample was determined strictly in accordance with the manufacturer's instructions via a standard measured at the same time. The interassay variance in the normal and increased region was less than 10% CV.

The Roche Elecsys™ PTH assay is an electrochemiluminescence immunoassay (ECLIA) on the fully automatic immunoanalyzer Elecsys $^R$2010. The epitope recognized by the biotinylated captor antibody contains the PTH amino acids 26 to 32 and the monoclonal ruthenium detection antibody recognizes, in accordance with the information from the manufacturer, an epitope in the region of the PTH amino acids 55 to 64. Sample and antibodies were incubated together for 9 minutes at 37° C., Streptavidin coated paramagnetic beads introduced to the incubation mixture, and finally incubated for further 9 minutes. After magnetic separation of the bonded conjugates from the free conjugates on an electrode surface the luminescence was determined and the end PTH concentration determined via a recalibrated master curve. The interassay variance in the lower and upper normal region was less than 7% CV and in the high concentration region 5% CV.

For the oxidation and reduction experiments standards and pool plasmas from dialysis patients having hPTH (1-37) fragments of different concentrations and oxidation states were treated. All samples received EDTA as anticoagulant. The measurement of the native, unaltered initial samples (reference parameter) and of the treated pool plasmas was effected at the same time. The determinations were effected in each case strictly in accordance with the manufacturer's instructions.

1. Standard Experiment

PTH IRMA standard of the company Nichols Institute having a nominal concentration of 46.8 pmol/l.

2. Experiment with Plasma Pools

Two separate samples of EDTA plasma samples from dialysis patients having increased content of intact PTH were pooled.

| Pool | PTH intact Elecsys | PTH intact Nichols |
|---|---|---|
| Pool 1 | 76.7 pmol/l | 59.2 pmol/l |
| Pool 2 | 72.4 pmol/l | 54.5 pmol/l |

The standard sample and the plasma pools where in each case treated with three different concentrations of hPTH(1-37) fragments in five different oxidation and state forms and then the recovered PTH contents determined.

Two treated PTH(1-37) fragment solutions received native hPTH(1-37) from various manufacturers (1: IPF=Institut für Peptidforschung, Braunschweig, 2=Immundiagnostik AG, Bensheim). In the third fragment solution of hPTH(1-37) the methionine at position 8 was oxidized, in the fourth the methionine at position 18 and in the fifth both methionines at positions 8 and 18 were oxidized.

There were produced from each fragment solution three initial concentrations (1000 nM, 100 nM and 10 nM). A further dilution of the fragment solutions 1:100 in the standard and in the pool plasma yielded final concentrations of 10000 pMol, 1000 pMol and 100 pMol in the sample to be analyzed. There were employed in each case three fragment concentrations because the binding capacities of the captor antibodies employed in the commercial tests against the N-terminal PTH fragment were not known. The aim of the experiment was to completely occupy the captor antibodies with native or oxidized hPTH(1-37), so that they are no longer available for forming the sandwich complex and the measurement signal fell below the respective detection limit. The comparison of the measurement values from samples having added native hPTH(1-37) fragments or added oxidized fragments then provides information on the specificity of the captor antibodies. The results are summarized in the diagram shown in FIGS. 1 to 4.

For calculating the blockage of the N-terminal antibodies, the measured concentrations of the standard and of the pool plasmas were treated with the native PTH preparation hPTH (1-37) from IPF were determined to be 100%, and all further values placed in relationship thereto.

Discussion of the Results with the Elecsys™2010 PTH Test

See diagrams of FIGS. 1 and 2. On the basis of the minimal percentage deviations of the measurement values of all PTH fragments, oxidized at different positions, it can be assumed that the Roche Elecsys™2010 test recognizes the oxidized PTH only with slight affinity and mainly reacts with native and thus biologically active parathyroid hormone. The absence of signal reduction even with the very high fragment concentration of 10 000 pM speaks for an extremely high binding capacity of the captor antibody. The native measured samples lay in absolute concentration a maximum of 10% higher than the corresponding treated samples. With the Elecsys™2010 PTH test it however remains disadvantageous that directly produced active N-terminal PTH fragments are not detected, since the tracer antibody binds in the C-terminal section of the PTH; on the other hand, however, biologically inactive PTH(4-37)-fragments, which are lacking the N-terminal epitope with the amino acids 1 to 3, are partially detected.

Discussion of the Results with the Nichols IRMA PTH Test

See the diagrams of FIGS. 3 and 4. Differently than with Elecsys™2010 PTH test the spiking experiments with the IRMA intact PTH test produced clear differences in reaction behaviour depending upon the addition of the various fragments. The standard employed also behaved differently to the pool plasmas, which may be due to the different matrix (protein content etc.). The visible signal reduction with a concentration of 1000 pM hPTH(1-37) to 50% of the native measured sample shows the lower binding capacity of the captor antibody against the N-terminal PTH fragment. The non-oxidized hPTH(1-37) fragments from IPF and Immundiagnostik behave differently, whereby the difference is particularly clear in the case of the pool plasmas. Also the measurement signals fell clearly as soon as oxidized hPTH (1-37) fragments were added. On the basis of the results it can be assumed that the polyclonal antibody material employed in the test kit of the Nichols Company contains various antibody populations which react both with native and also with oxidized PTH. The different binding behaviour of the various oxidized hPTH(1-37) fragments is interesting. It is to be checked whether the various oxidized molecules (at position 8 or 18 or both positions) have different biological effects.

With the experiment it could be shown that with the polyclonal antibody material (Nichols IRMA), in contrast to the monoclonal antibodies (Elecsys 2010), along with native PTH also oxidized inactive PTH forms were detected. The oxidized PTH has for the target cells for calcium homeostasis (kidney, bone) a restricted to no biological activity.

Example 3

Oxidation and Reduction of Plasma Samples of Uraemic Patients

In dialysis, dialysis patients are exposed to an increased oxidation stress. It was thus investigated whether an oxidation of the PTH occurs in vivo—with corresponding consequences for its biological activity. It was further investigated whether and to what extent a direct oxidation or a reduction or reverse reduction of the PTH molecules in the samples is possible.

30 plasma samples of dialysis patients and ESRD patients (ESRD=end stage renal disease) were selected at random and oxidized with hydrogen peroxide (30%; end concentration: 1.5 Mol/L) or reduced with sodium boron hydride (NaBH$_4$, aqueous solution of 100 nMol/L). All samples, treated and untreated, where measured at the same time with the Roche Elecsys™2010 and the Nichols IRMA test.

The oxidation was effected with 30% hydrogen peroxide solution. The hydrogen peroxide concentration in the incubation preparation was at 17% of the 30% solution. All samples were incubated for 45 minutes at 37° C., then also cooled down to −70° C., lyophilized and stored at −20° C. until the quantitative PTH determination.

Of 20 samples an aliquot of each in the ratio 1:1 (v/v) was treated and reduced with a 100 nMol NaBH$_4$ solution. Further, of 10 oxidized samples in each case an aliquot was reverse reduced by the addition of a 100 nMol NaBH$_4$ solution in the ratio 1:1. The samples were incubated for 45 minutes at room temperature and the reaction stopped on dry ice. After the lyophilization the samples were deep frozen at −20° C. until determination. The diagrams of FIGS. 5 to 11 show the results.

See FIGS. 5 and 6. The measurement values obtained with the Roche Elecsys™2010 test for native PTH lay, after the oxidation, on average at 29% of the initial value. Here, the individual samples behaved very differently. The maximum reduction of the measurement signals was 10% and the minimal reduction of the measurement signal was 53% of the initial value. The result show that the captor antibody used in the Roche Elecsys™2010 PTH test mainly recognizes the native, reduced PTH form.

See FIGS. 7 and 8. The oxidation has clearly lesser influence on the measurement values in the Nichols IRMA. On average, the concentration reduced to 76% of the initial value with a maximum reduction to 33% in a minimal reduction 98%.

In order to exclude a partial destruction of the PTH molecule as a result of the pre-treatment of the samples with H$_2$O$_2$, the oxidized samples were reverse reduced again with NaBH$_4$. Upon measurements of the reverse reduced samples with the Elecsys™2010 PTH test only ca. 50% of the initial value could be attained. Since the detection system is however based on an electrochemical luminescence reaction, the reduction medium probably disrupted determination. In further experiments a disruption of the measurement signal in the Elecsys system was found also with other antioxidants. Probably, however, also a proportion of the methionine was oxidized to sulfone, which cannot be reverse reduced.

FIGS. 9 and 10 show the results in the parallel experiments with the Nichols IRMA. The results show that the oxidation or reduction of the peptide does not influence the immunological activity. After oxidation and corresponding reverse reduction the native initial concentrations were largely attained. The slight differences in the recovery after the reverse reduction are probably due to different (oxidation) initial conditions of the peptide.

FIG. 11 shows the results for the sole reduction of native PTH. The sole reduction leads to a slightly increased recovery (plus 4%) of the native initial value. The polyclonal antibodies employed in the Nichols test, with their higher affinity for the oxidized form of the peptide, probably prevent a detectable accented manifestation of different PTH concentrations before and after reduction of the peptide.

The data shows clearly the influence of an oxidation on the concentration of intact PTH measured with various tests. Native and oxidized PTH show significant differences in the biological activity on various target organs. In particular dialysis patients are clearly exposed to a high oxidative stress and the suspicion lies to hand that free reactive oxygen species significantly change the parathyroid hormone, through oxidation of methionine in its structure and thus significantly changes the biological activity. Thus, dialysis patients often suffer from hyperhomocystinemea, a known indicator for oxidation stress and a disrupted homocystine metabolism (Durand P. et al. Laboratory Investigation 2001, 81(5), 645-672). In the parathyroid hormone the methionines at positions 8 and 18 are above all susceptible to oxidation. The oxidation of the methionines at positions 8 and 18 to methionyl sulfoxide is probably biologically reversible due to the methionyl sulfoxide reductase occurring in the tissues (Vogt W., Free Radical Biology & Medicine, 1995, 18(1), 93-105). It leads certainly to a loss of physiological effect (Galceran et al, Endocrinology, 1984, 115(6), 2375-2378; Horiuchi N. J. Bone Miner. Res., 1988 3(3), 353-358), Zull J E et al., J. Biol. Chem., 1990265(10), 56715676; O'Riordan J L H et al., J. Endocr., 1974, 63, 117-124). Thus, the tests available at the present time cannot differentiate biologically active PTH from inactive PTH.

Example 4

Selective Blocking of the N-Terminal Binding Site of Oxidized PTH Through the Addition of Monoclonal Antibodies Against Oxidized PTH There was employed a monoclonal antibody against oxidized PTH in accordance with Logue F C et al. (Annu. Clin. Biochem. 1991, 28, 160-166; J. Immunol. Methods, 1991, 137, 156-166). Briefly, this was obtained in that synthetic hPTH(1-34) was oxidized by the addition of hydrogen peroxide (30%) and then DA rats were immunized with this. There may also be effected an immunization with synthetic PTH fragments (1-37) which contain a methionyl sulfoxide at positions 8 or 18. The fusion of the rat spleen cells with the mouse myeloma line X63Ag8.653 then delivers various monoclonal antibodies which were tested in an immunoassay for their characteristics for binding and masking oxidized PTH.

FIGS. 12 and 13 show elimination experiments with a monoclonal antibody mAK-hPTH(1-37)-metox-8/18 (3B3), which recognizes an epitope having PTH methionyl sulfoxide. For comparison purposes, this antibody was employed in a conventional PTH IRMA of the Nichols Institute and in the Elecsys™200 PTH of the company Roche.

For this purpose there were produced 10 EDTA plasma pools with mean PTH values in the high concentration region (mean value±SD: NID 46±17 pMol/L; Roche 41±14 pMol/L) and for blocking the N-terminal binding site were treated with the above-described monoclonal antibody against oxidized PTH. For this purpose, the samples were so mixed with a solution of the monoclonal antibody that the final concentration in the sample with regard to the monoclonal antibody was at 200 ng/ml or 20 ng/ml. The sample was preincubated for one hour at room temperature with the masking antibody against oxidized PTH and then subjected to determination in conventional manner with the respective test kit from Roche or Nichols. The results are illustrated in FIGS. 12 and 13.

Here, NID and R stand for the Nichols or Roche test and "neat" for untreated samples, 200 for the addition of 200 ng/ml mAK-hPTH(1-37)-metox-8/18 (3B3) masking antibody, 20 for the addition of 20 ng/ml masking antibody, Rox or NIDox for a hydrogen peroxide oxidized sample according to Example 3, and 200 or 20 for the indicated dose of masking antibody.

The results show that the PTH assay of the Nichols Institute cannot distinguish between oxidized inactive PTH and native active PTH, but that through the addition of masking antibodies against oxidized PTH—even with a polyclonal goat antibody against hPTH(1-34)—an antibody binding in the N-terminal section and an incorrect determination can be suppressed to the widest degree. The experiments further show that even normal pool plasmas contain ca. 10% oxidized PTH.

The Roche PTH test contains a conformation detection antibody (PTH 55-64) which can apparently distinguish between oxidized and native-active PTH. However, through the addition of masking antibodies falsely excessive determinations, in particular in the untreated sample, are clearly reduced.

It is to be noted that both comparison tests detect no active PTH fragments of the type hPTH(1-34v37) and thus deliver immanently false PTH contents.

The invention claimed is:

1. A method of determining the concentration of biologically active human parathyroid hormone in a physiological sample, wherein said method comprises:
    contacting a first antibody with a sample, wherein said sample comprises a body fluid, wherein the first antibody specifically recognizes human parathyroid hormone polypeptide chains and fragments thereof which comprise oxidized residues at methionine 8 and/or methionine 18;
    contacting a second antibody with the sample, wherein said second antibody specifically recognizes an epitope formed by the N-terminal amino acids 1 to 3 of the human parathyroid hormone polypeptide chains; and
    contacting a third antibody with the sample, where the third antibody specifically recognizes an epitope within amino acids 15 to 22 of the human parathyroid hormone polypeptide chains,
    whereby human parathyroid hormone comprising oxidized methionine residues are precluded from detection by binding of the first antibody, which blocks the second antibody and/or third antibody from binding to oxidized parathyroid hormone polypeptide chains and fragments thereof,
    thereby determining the concentration of biologically active human parathyroid hormone recognized by the second and third antibodies.

2. The method according to claim 1, wherein the first antibody masks oxidized parathyroid hormone and its fragments, such that exclusively reduced, biologically active parathyroid hormone and its fragments are detected.

3. The method according to claim 1, wherein the method further comprises adding from 0.05 to 0.1 weight % of a mild detergent to the sample.

4. The method according to claim 1, wherein the first antibody is a monoclonal antibody.

5. A method of determining the concentration of reduced biologically active human parathyroid hormone (hPTH) in a physiological sample, wherein said method comprises:
    dividing a sample into two sample aliquots;
    contacting a first antibody with a first sample aliquot wherein the first antibody specifically recognizes hPTH polypeptide chains and fragments thereof which comprise oxidized residues methionine 8 and/or methionine 18, and determining a concentration of oxidized human parathyroid in the sample aliquot;
    contacting a second antibody with a second sample aliquot, wherein the second antibody specifically recognizes an epitope formed by N-terminal amino acids 1 to 3 of hPTH polypeptide chains;
    contacting a third antibody with the second sample aliquot, wherein said third antibody specifically recognizes an epitope within amino acids 15 to 22 of human parathyroid hormone polypeptide chains;
    determining the total concentration of oxidized and reduced hPTH in the second sample aliquot; and
    calculating the concentration of reduced, biologically active hPTH in the second sample from the total oxidized and reduced concentration of hPTH in the second sample and the concentration of oxidized hPTH in the first sample.

6. The method according to any one of claims 1-4, wherein the second antibody or the third antibody comprise a detectable marker, wherein said marker is selected from the group consisting of: a fluorescing group a chemiluminescing group and an enzyme for catalysis of a detection reaction.

7. The method according to any one of claims 1-4, wherein the second antibody or the third antibody is biotinylated.

8. The method according to any one of claims 1-4, wherein the third antibody is a monoclonal antibody, and wherein the third antibody comprises a ruthenium complex, and wherein the third antibody recognizes an epitope in the region of the amino acids 15 to 22 of human parathyroid hormone.

9. A method of determining the concentration of biologically active human parathyroid hormone in a physiological sample, wherein said method comprises:
    providing a sample, wherein said sample comprises a body fluid;
    contacting the sample with a first antibody, wherein the first antibody specifically recognizes human parathyroid hormone polypeptide chains which are oxidized at methionine 8 and/or methionine 18;
    determining the amount of intact parathyroid hormone peptide chains and N-terminally intact fragments thereof in said sample by sandwich immunoassay, wherein said sandwich immunoassay comprises a second antibody and a third antibody, and wherein one of the second antibody or third antibody specifically binds to the receptor-binding site within amino acids 15 to 22 of the human parathyroid hormone polypeptide chain, and the other one of the second antibody or third antibody binds to either an epitope formed by amino acids 1 to 3 of the human parathyroid hormone or to the middle or C-terminal section of the human parathyroid hormone polypeptide chain,
    whereby human parathyroid hormone comprising oxidized methionine residues are precluded from detection by binding of the first antibody, which blocks the second antibody and/or third antibody from binding to oxidized parathyroid hormone polypeptide chains and fragments thereof,
    thereby determining the concentration of biologically active human parathyroid hormone.

10. The method of claim 9, wherein the respective second or third antibody which binds to the middle or C-terminal section of the human parathyroid hormone polypeptide chain recognizes an epitope within amino acids 53 to 68 of the human parathyroid hormone polypeptide chain.

11. The method of claim 9, wherein the respective second or third antibody which binds to the middle or C-terminal section of the human parathyroid hormone polypeptide chain recognizes an epitope within amino acids 53 to 84 of the human parathyroid hormone polypeptide chain.

* * * * *